United States Patent
Kinast et al.

(10) Patent No.: US 7,617,718 B2
(45) Date of Patent: Nov. 17, 2009

(54) DEVICE AND METHODS FOR USE OF A DYNAMIC CONE PENETROMETER FOR EVALUATING SOIL COMPACTION

(75) Inventors: John Arthur Kinast, Chicago, IL (US); Khalid A. Farrag, Streamwood, IL (US); H. A. (Alan) Todres, Skokie, IL (US)

(73) Assignee: Sandy Golgart Sales, Inc., Addison, TX (US)

( * ) Notice: Subject to any disclaimer, the term of this patent is extended or adjusted under 35 U.S.C. 154(b) by 193 days.

(21) Appl. No.: 11/610,342

(22) Filed: Dec. 13, 2006

(65) Prior Publication Data

US 2007/0131025 A1    Jun. 14, 2007

Related U.S. Application Data

(60) Provisional application No. 60/749,863, filed on Dec. 13, 2005.

(51) Int. Cl.
*G01N 3/34* (2006.01)
(52) U.S. Cl. .............................................. 73/84; 73/85
(58) Field of Classification Search .................. 73/82, 73/84, 784, 12.01, 12.04, 12.13, 85
See application file for complete search history.

(56) References Cited

U.S. PATENT DOCUMENTS

| 2,117,985 A | * | 5/1938 | Ridenour ........................ 73/84 |
| 3,998,090 A | * | 12/1976 | Wislocki ...................... 73/12.12 |
| 4,061,021 A | * | 12/1977 | Baldwin et al. ................. 73/84 |
| 4,353,247 A | * | 10/1982 | De Domenico ................ 73/84 |
| 4,480,481 A | * | 11/1984 | Buchele ........................ 73/784 |
| 4,531,400 A | * | 7/1985 | Nevel ........................ 73/12.13 |
| 4,640,120 A | * | 2/1987 | Garritano et al. ........... 73/12.13 |
| 5,313,825 A | * | 5/1994 | Webster et al. .................. 73/81 |
| 5,390,535 A | * | 2/1995 | Smock et al. .................. 73/79 |
| 5,426,972 A | * | 6/1995 | Heirtzler et al. ................ 73/84 |
| 5,454,264 A | * | 10/1995 | Lampinen et al. .......... 73/12.06 |
| 5,457,984 A | * | 10/1995 | Ambur et al. .............. 73/12.09 |
| 5,663,649 A | * | 9/1997 | Topp et al. ................... 324/643 |

(Continued)

FOREIGN PATENT DOCUMENTS

DE        3728669 A1 *  3/1989

OTHER PUBLICATIONS

Herrick et al., "A Dynamic Cone Penetrometer for Measuring Soil Penetration Resistance," Soil Sci. Soc. Am. J., 66:1320-1324 (2002).*

(Continued)

*Primary Examiner*—John Fitzgerald
(74) *Attorney, Agent, or Firm*—Husch Blackwell Sanders Welsch & Katz; George S. Pavlik (57) ABSTRACT

The present invention includes a device and method for more particularly evaluating the compaction of soil by automating the use of a prior art dynamic cone penetrometer such that user error and error caused by field conditions are eliminated. Recordation of penetrometer data previously not recorded is made more precise by the present invention such that standardized measurement results. The device further includes means for facilitating the determination of compaction of soils through keyhole openings and a means for automating the collection and processing of the generated compaction data.

8 Claims, 10 Drawing Sheets

U.S. PATENT DOCUMENTS

| | | | | |
|---|---|---|---|---|
| 5,686,652 | A * | 11/1997 | Pfund | 73/12.04 |
| 5,726,349 | A * | 3/1998 | Palmertree et al. | 73/84 |
| 6,536,263 | B1 * | 3/2003 | Wood et al. | 73/82 |
| 6,647,799 | B1 * | 11/2003 | Raper et al. | 73/784 |
| 6,925,858 | B2 * | 8/2005 | Miles et al. | 73/84 |
| 6,973,822 | B1 * | 12/2005 | Sawyers | 73/82 |
| 6,983,643 | B2 * | 1/2006 | Brighton et al. | 73/81 |
| 7,137,285 | B2 * | 11/2006 | Stroppiana | 73/12.13 |
| 7,299,686 | B2 * | 11/2007 | Briaud et al. | 73/84 |
| 2005/0178184 | A1 * | 8/2005 | Stroppiana | 73/12.13 |
| 2007/0046289 | A1 * | 3/2007 | Troxler | 324/334 |
| 2007/0277598 | A1 * | 12/2007 | Zacny et al. | 73/84 |

OTHER PUBLICATIONS

Jones et al.: "Guide to Sampling Soil Compaction Using Hand-Held Soil Penetrometers," Ctr. Env. Mgmt of Mil. Lands., Jan. 2004.*

* cited by examiner

DEVICE AND METHODS FOR USE OF A DYNAMIC CONE PENETROMETER FOR EVALUATING SOIL COMPACTION

REFERENCE TO RELATED APPLICATION

This application is related to U.S. Provisional Patent Application Ser. No. 60/749,863 filed Dec. 13, 2005 entitled "Automation Of Testing, Recording, And Determination Of Acceptable Status Utilizing A Dynamic Cone Penetrometer (DCP)", the entirety of which is incorporated as if set forth in its entirety herein.

BACKGROUND OF THE INVENTION

Penetrometers and related devices have been used for a variety of geotechnical engineering purposes over the years. Among the well-known types of penetrometers is the utility dynamic cone penetrometer ("DCP") which is commonly used by utility companies to determine the adequacy and degree of soil compaction in restorations of openings made in roadways or other land features for the purpose of installing or maintaining underground facilities. Other types of DCPs are also presently known to be used in evaluating parameters in addition to soil compaction, including for example resistance to penetration or shear strength.

Generally, DCPs consist of an elongated shaft having a first and second flange spaced a standardized distance apart with a standardized drop weight conveyed freely there-between on the shaft. The DCP further has a conically shaped tip that is driven into the soil by means of the drop weight being lifted to the height of the first flange and then dropped onto the anvil, or second flange, attached to the shaft. Typically, the drop weight of most DCPs has a standardized mass and a standardized range of movement along the shaft, and thus the driving energy caused by the drop weight striking the anvil is also standardized. In common usage, the operator of the DCP will position the tip of the penetrometer on a soil to be evaluated and with one hand will raise the weight up to the first flange, which is located below a handle provided for steadying the device with the other hand. The weight is then released and permitted to fall freely by gravity. The driving energy generated by the weight hitting the anvil causes the tip of the DCP to move in a downward direction into the soil. Generally, the process of raising and releasing the weight to strike the anvil will be repeated until a standard depth of penetration is established. At that time a record is made of the number of times the anvil has been raised and dropped, as an indication of the relative compactness of the soil. If the required blowcount is reached before the standard penetration is reached, this automatically means a passing condition, and further blows are unnecessary, and not usually pursued.

The utility DCP is usually used in a go/no-go fashion, in which the number of blows by the drop weight to the anvil to achieve a standard depth of penetration is compared with a predetermined standard: if the number of blows equals or exceeds the standard, the compaction of the soil is deemed adequate. If the number of blows, however, does not meet or exceed the predetermined standard, additional compaction of the soil is performed until the standard is met. Certain soils may require a different criterion; one such is poorly-graded sand, for which the blow-count is determined for a greater depth of penetration, and thus one or more additional gradation lines can be provided on the shaft near the tip to assist in determining appropriate compaction.

DCPs are generally manual testing devices, relying exclusively on the ability of the user to record test results. Automation approaches by others in the field of soil testing, involve the use of some electronic measuring assemblies attached to the DCP. One such implementation involves a linear variable differential transformer sensor (e.g., an LVDT sensor) that extends from the DCP to the soil. Another implementation, by Applied Research Associates, Inc. ("ARA") (marketed by Vertek as a Data Acquisition System ("DAS")), features a portable DAS that utilizes a string potentiometer attached to a hook on the DCP rod anvil in such a way as to monitor the DCP penetration. These presently known automated approaches however are generally cumbersome and fragile and further lack the ability to readily transmit data collected by the DCP to remote data-logging and display devices, such as portable computers or personal digital assistants ("PDAs") for secure logging and retention of data. Existing automated approaches are also generally unable to effectively display the collected data in real-time or transmit the data by means of wireless transmitters.

Accordingly, there is a need for an automated device and method to relieve a user of a DCP from the arduous task of keeping track of data manually. It would thus be advantageous to have a device to alleviate the need for the user to manually measure the distance that the DCP has moved during a particular evaluation, and further that would free the user from having to manually count the number of times that the drop weight strikes the anvil. It would additionally be advantageous if such an innovation could determine whether the drop weight of the DCP has been raised to an appropriate position before being released in order to generate the standardized driving force. Such an innovation would ensure that the evaluation being carried out by the DCP is proper and would alert the user when certain drops of the weight were invalid and require repetition of the test. Use of such an automated device and method in connection with a DCP would lessen the likelihood of user error and thus provide a more accurate and reliable assessment of the compaction of soil being evaluated. An automated device and method of collecting data generated by a DCP would further provide a more permanent, secure and tamper-proof record for test data, including, but not limited to, data concerning site location, soil description, lift thickness, and blowcount and depth of penetration patterns.

Another difficulty in determining soil compaction (and/or other soil properties) is posed by the smaller openings, such as keyhole openings, that have begun to be used by utility companies, and others, in operations that require installation or repair of underground equipment or settings. Keyhole openings are typically smaller than 18-inches in diameter (when circular) or on a side (when rectangular). These openings have become feasible due to the development of tools allowing work to be performed on underground facilities from the surface through tight or enclosed spaces. As operators cannot physically enter such openings, compaction and verification of soil at the bottom of the opening must be performed from the surface above and outside of the so called "keyhole". The DCPs of the prior art as presently configured cannot be used for this purpose as readings are almost impossible to be made with any accuracy due to the limited sight lines available.

Accordingly, it would also be desirable to have a device and method to enable use of a DCP in a keyhole or in other applications in which a DCP is to be used to evaluate soil at the bottom of a small opening. It would be further advantageous for such a device and method to be automated in order to simplify the collection, recordation, monitoring and transmission of compaction data generated by the DCP so that it can be evaluated in real-time by the user and others from a remote location, and so that the data can be transferred to and stored at a centralized database for comprehensive record keeping, or transmission to others for analysis.

SUMMARY OF THE INVENTION

In one embodiment of the present invention, an automated device for processing soil compaction data generated by a dynamic cone penetrometer ("DCP") is provided. The automated device features a sensor assembly having a distance sensing means, data acquisition means, and a transmitter. The device further includes a display device, a recording device, and a receiver for receiving data from the transmitter. A processing device in communication with the receiver is further provided for processing the data communicated to the receiver and to communicate the processed data to the recording device and the display device.

In this embodiment, the distance sensing means can be an optical or ultrasonic distance sensor and the processing device can be a handheld computer, a laptop computer, a cell phone or a personal digital assistant (PDA). Further, the transmitter of the automated device can be a radio frequency transmitter, an infrared light transmitter, a Bluetooth® or equivalent wireless protocol signal transmitter or other short range telemetry protocol transmitter.

Another embodiment of the present invention is directed to a DCP for automated evaluation of soil compaction. In this embodiment, the DCP features an elongated shaft having a first end with a flange and a handle adjacent to the flange and a second end comprising a tip. The elongated shaft may further feature a graduated area having one or more horizontal markings positioned in generally vertical alignment to one another along the length of the shaft near the tip. The flange of the DCP extends in a direction perpendicular to the elongated shaft and an anvil is fixedly mounted between the first and second ends of the elongated shaft. The DCP also features a drop weight slideably mounted to the elongated shaft such that the weight is moveable along the shaft between the flange and the anvil. In this embodiment, an automated device for collecting and processing compaction data from the DCP is also featured. Like the previously described embodiment, the automated device can comprise a sensor assembly having a distance sensing means, data acquisition means, and a transmitter. The device further includes a display device, a recording device, and a receiver for receiving data from the transmitter. A processing device in communication with the receiver is further provided for processing the data communicated to the receiver and to communicate the processed data to the recording device and the display device.

The DCP of this embodiment can further include an automated system for detecting when the drop weight has been raised into an upper position above the anvil. This system features a weight detection assembly positioned between the first end of the DCP and the anvil and a remote operator assembly having a receiver and an electronic processing device. The detection assembly of the system can further have a detector and transmission element tuned to receive and process compaction data. When the drop weight of the DCP is raised into the upper position, the detector is actuated in a manner which generates a signal that is broadcast by the transmission element to the receiver of the remote operator assembly. The receiver can be adapted to receive the signal broadcast from the transmission element and to transfer the signal to the electronic processing device for processing, display or recording.

In this embodiment, the detector of the weight detection assembly comprises a switch that is actuated when the drop weight is raised into the upper position. The switch can be an optical distance sensor, an ultrasonic proximity switch or a physically or electrically actuated sensor. Alternatively, if the drop weight of the DCP comprises a magnetic field, the detection assembly can be an inductive sensor that detects when the weight is in the upper position by detecting the magnetic field.

Another embodiment of the present invention is directed to a DCP for automated evaluation of soil compaction through a keyhole type opening. In this embodiment, a DCP is provided having general features consistent with the DCP of the previous embodiment. The DCP of this embodiment further includes an adjustable collar adapted to fasten around the elongated shaft. The collar is movable on the shaft between the anvil and tip and can have cooperative graduations of comparable dimension to the height of the tip and also the markings of the graduated area on the elongated shaft near the tip. The cooperative graduations of the adjustable collar enable an operator to manually determine how deep the DCP has moved into the soil from outside the keyhole opening by enabling the operator to visually read the graduations against an apparatus placed horizontally across the top of the keyhole opening.

The DCP of this embodiment can also include at least one elongated shaft extension unit having a first and second ends that are both capable of fastening to the second end of the elongated shaft, the tip, or the first or second ends of another extension unit. The DCP of this embodiment can further be used in connection with a surcharge weight having a top and bottom surface with centrally located openings forming a central cavity that permits the tip and elongated shaft or a shaft extension unit to extend through the weight. An automated device for collecting and processing compaction data from the DCP can further be included in this embodiment, as can an automated system for detecting when the drop weight has been raised into an upper position above the anvil.

An automated method to collect, record and monitor compaction data generated by a DCP is further provided by one embodiment of the present invention. This method features placing a sensor assembly having an optical distance sensor and transmitter at a fixed position on a soil surface to be evaluated by the DCP. The DCP having a sensor target mounted to the elongated shaft is positioned such that the target is aligned with the assembly in a vertical plane. The distance between the sensor and the target is then detected and streamed as an electronic signal from the transmitter to a receiver mounted to a remote electronic processing device. The streamed signal from the transmitter can then be monitored as a value in real-time at the remote processing device such that the value remains constant where the distance between the sensor and the target does not change. The drop weight affixed to the penetrometer is then raised from a first position adjacent to the anvil to a predetermined second position above the anvil and then is released and permitted to fall under the force of gravity in a direction towards the anvil until the weight contacts the anvil. The contact generated by the weight striking the anvil generates a force that causes the penetrometer to move in a downward direction into the ground surface to be evaluated such that the distance between the target and sensor decreases. When this occurs, the value monitored by the remote processing device changes such that a new value is constantly displayed which corresponds to the new distance between the sensor and the target. The number of times that the value changes is then registered as the number of times that the weight strikes the anvil. The distance that the penetrometer moves after each blow by the anvil is recorded, as is the cumulative distance that the penetrometer has moved during the evaluation. This distance data provides a permanent record which can be viewed by the user or others so that the success or failure of the compaction evaluation can be determined.

In another embodiment of the present invention, an automated method is provided for detecting when the drop weight has been raised to an appropriate position along the shaft of the DCP. In this method the drop weight of the DCP is raised from a first position adjacent to the anvil to a predetermined second position above the anvil, such that when raised into the second position, the drop weight is in closer proximity to the top flange of the penetrometer. The presence of the drop weight in the second position is detected by a weight detection assembly and an electronic signal indicating that the weight is present in the predetermined second position is generated. The electronic signal is transmitted to a reception element of a remote electronic processing device where a signal, such as for example an audible tone, can be generated in order to alert the user that the weight has been lifted into the second position. The drop weight is then released from the second position above the anvil and permitted to fall under the force of gravity in a direction towards the anvil. The absence of the drop weight in the second position is detected and an electronic signal is generated and transmitted upon release of the weight from the second position.

Another embodiment of the present invention is directed to a method of using a DCP to evaluate the compaction of soil through a keyhole type opening having an open top. In this method an apparatus having a top and bottom surface is placed across the open top of the keyhole opening. An adjustable collar is affixed to the elongated shaft in a position between the anvil and the tip. The DCP, possibly having one or more shaft extension units to match the height of device to the depth of the keyhole, is then positioned in the keyhole such that the tip of the DCP is resting on the soil surface at the bottom of the keyhole or is buried in the soil to a predetermined initial depth. The collar is then adjusted along the elongated shaft such that its cooperative graduated area can be read against the top surface of the apparatus spanning the opening of the keyhole. The drop weight affixed to the penetrometer is then raised from a first position adjacent to the anvil to a predetermined second position above the anvil and then released and permitted to fall under the force of gravity in a direction towards the anvil. A measurement is then taken to determine how much the DCP moved into the soil.

While the device and methods of the present invention are ordinary used in connection with evaluations for determining the compaction of various types of soil, persons having ordinary skill in the art will understand that each of the embodiments described herein may be used for alternative purposes, including for example evaluating resistance to penetration or shear strength, without departing from the novel scope of the present invention.

DETAILED DESCRIPTION OF THE INVENTION

While the present invention is susceptible of embodiment in various forms, there is shown in the drawings a number of presently preferred embodiments that are discussed in greater detail hereafter. It should be understood that the present disclosure is to be considered as an exemplification of the present invention, and is not intended to limit the invention to the specific embodiments illustrated. It should be further understood that the title of this section of this application ("Detailed Description of the Invention") relates to a requirement of the United States Patent Office, and should not be found to limit the subject matter disclosed herein.

Figure 1:
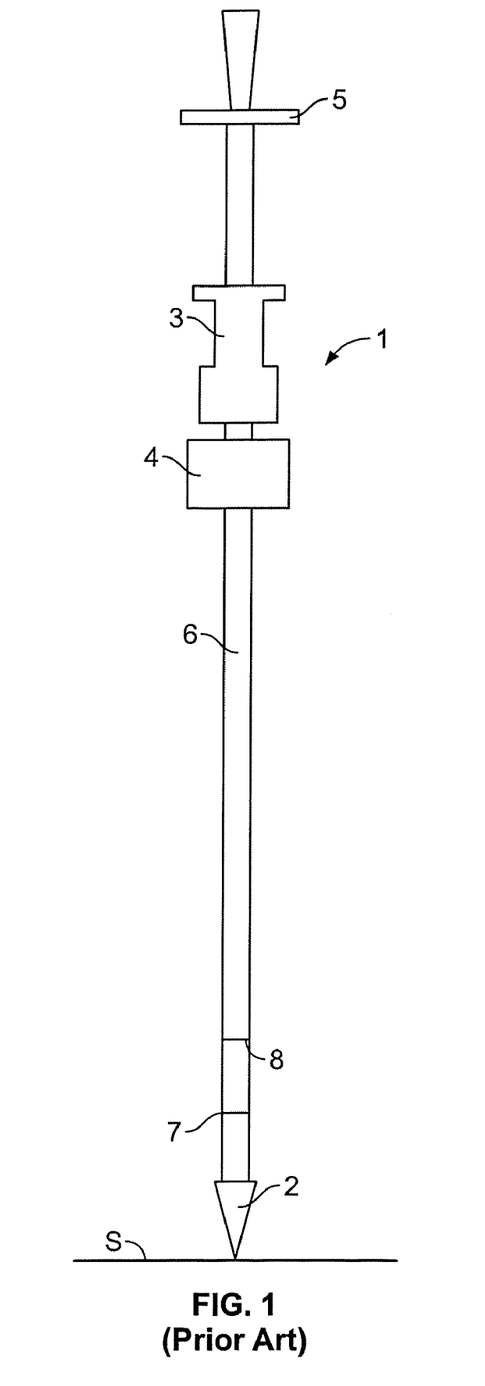
FIG. 1 is an elevational view of a Dynamic Cone Penetrometer ("DCP") of the prior art.

FIG. 1 shows a dynamic cone penetrometer ("DCP") 1 having general characteristics in accordance with the teachings of the prior art. Persons having ordinary skill in the art will understand the basic operations of such a device; however, briefly, the tip 2 of the device is generally placed onto the surface of soil "S" whose compaction is to be tested. A weight 3 is raised from the flange, or anvil, 4 on which it rests, up to an upper flange 5 and allowed to drop to its first at rest position. The dropping of the weight causes the cone 2 to penetrate the surface of the soil S. This operation is repeated until the tip 2, and attached shaft 6, penetrate the soil to a marked level (such as, for example, as graduated 7 or 8 on the shaft depending on the type of soil being evaluated). The number of drops of the weight to reach this level is recorded and serves as an indication of the compactness of the soil.

Figure 2:
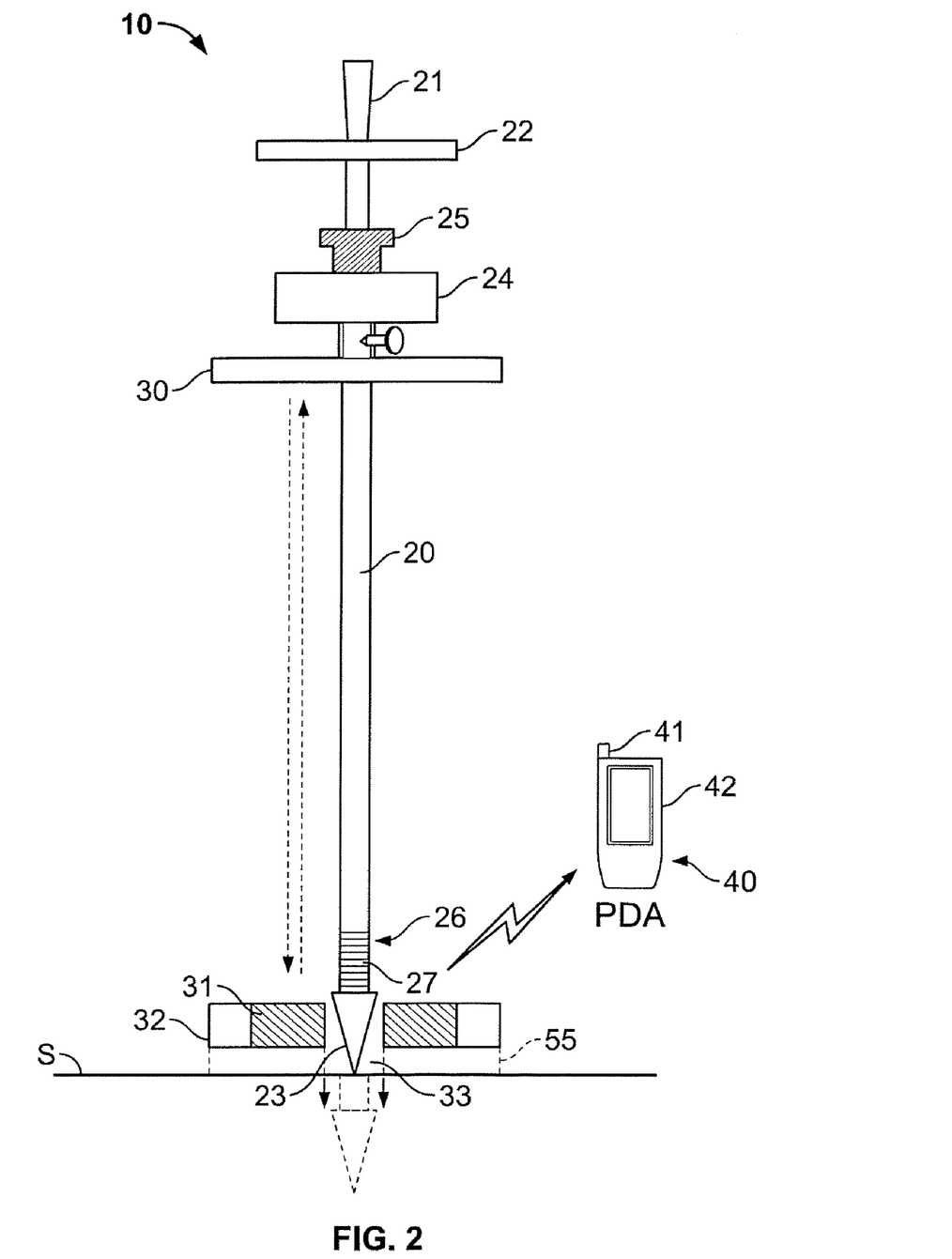
FIG. 2 is an elevational view of one embodiment of a device made in accordance with the teachings of the present invention, including a sensor assembly for automatically collecting, transferring and monitoring data generated by a DCP.

In FIG. 2, an embodiment of the present invention designed to automatically collect, transfer and monitor the data generated by a DCP 10 is provided. As shown in FIG. 2, the DCP 10 features an elongated shaft 20 with a handle 21 and flange 22 at one end, and a conically shaped tip 23 at the other end. It will be understood by persons having ordinary skill in the art that while the various parts shown have been described and illustrated as having certain shapes, the actual shapes of the parts, such as "conical", are merely given for ease of understanding, and that various shapes, sizes and proportions can be interchanged without departing from the novel scope of the present invention. For example, the tip of the device can have any shape that advantageously permits the end of the DCP to penetrate the soil while working, such shapes as generally triangular and others can be substituted therefore.

The handle 21, in the illustrative embodiment, is located adjacent to a flange 22 and extends generally perpendicularly about shaft 20. The DCP 10 also has an anvil 24 and drop weight 25, having a standardized mass, mounted so that it can ride freely along shaft 20. The drop weight 25 is slideably mounted to the elongated shaft 20 in a manner that allows the weight 25 to be manually or mechanically raised from a lower position adjacent to the anvil 24 to an upper position proximate to the handle 21.

In the present embodiment, the elongated shaft 20 may also have a graduated area 26 to permit the measurement of the depth-of-penetration that is achieved once the tip 23 is driven into the ground surface "S" to be evaluated. The graduated area 26 can feature one or more horizontal markings 27 positioned in generally vertical alignment along the length of the shaft 20 proximate to the conically shaped tip 23. In normal "go/no go" operation of the DCP, the user is generally interested in determining whether a standard depth of penetration can be achieved by at least a required number of blows by the drop weight. The markings 27 of the graduated area 26 correspond to standard penetration depths of various soil types and are thus provided along the shaft in order to assist the user in determining when a standard depth of penetration has been achieved.

Figure 2A:
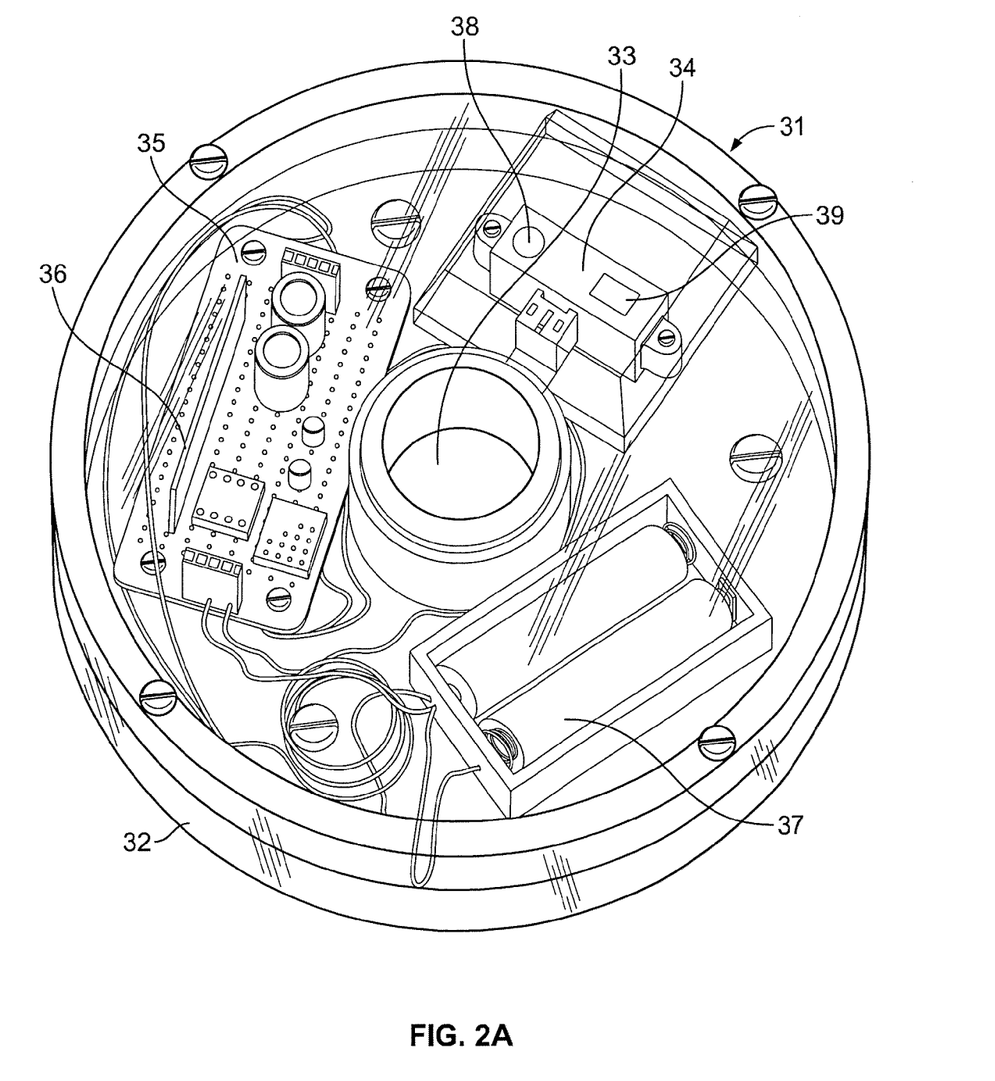
FIG. 2A is a top perspective view of one type of sensor assembly of a type shown in FIG. 2.

In use, the DCP 10 of the present embodiment is positioned such that the tip 23 is placed on the ground surface S to be evaluated. Often the initial position of the tip 23 for evaluation is such that the end of the tip adjacent to the shaft 20 is flush with the soil S. This position is usually achieved by initially tapping the weight 25 against the anvil 24 until the tip 23 is sufficiently buried in the soil S. After being raised to the desired upper position, drop weight 25 is released and permitted to fall onto anvil 24. As will be understood by persons having ordinary skill in the art, the contact between the drop weight 25 and the anvil 24 generates a standardized force that causes DCP 10 to move in a downward direction into the ground surface S to be evaluated. In the present embodiment however, the DCP 10 also features an automated method and device for recording and collecting data generated by this action. As shown in FIGS. 2 and 2*a*, the device of the present invention includes a sensor target 30 mounted to the elongated shaft 20 between the anvil 24 and the conically shaped tip 23, a remote operator assembly 40, and a sensor assembly 31 mounted within a housing 32, having a centrally located opening 33 to enable the tip 23 of the DCP 10 to pass through the housing 32 and contact the soil surface S. The present embodiment can additionally feature a surcharge weight 55 that can be incorporated in housing 32 or be a separate item with an opening in approximate vertical alignment with the opening 33 of the housing 32.

In the operation of the device of the present embodiment, a weight 25 is raised and dropped onto the anvil 24 of the penetrometer as described above, with respect to the prior art. The sensor 34 records the distance that the DCP 10 is driven into the ground surface S each time the drop weight 25 contacts the anvil 24, and also measures the cumulative distance that the DCP 10 travels into the ground surface S, during a particular evaluation. The automated data collection method and device of the present invention includes means to collect the distance measurements as well as the number of times the weight 25 strikes the anvil 24, and also features means to broadcast the data collected to a desired receptor. In operation, therefore, as the penetrometer is used, the sensor 34 collects the measurements as data and then broadcasts the data as an electronic signal to the remote operator assembly 40 for information presentation and results recording.

It will be seen that the device of the present invention automates the process of independently documenting the number of blows to travel a known distance (instead of relying on the memory of the user). The device further provides additional important and useful information to the user which has previously been unavailable, such as the actual distance traveled per blow (review of which may help to identify uniformity of soil compaction, for example). The device can provide information that can help to independently identify whether a particular soil spot has been compacted to an acceptable level (passes) or not (fails the test). Use of the device can automate the recording of the details of tests providing specific detailed information for an entire construction site or over any operational area covered by a utility or its contractors, for example. Since the data collected by the present invention can be transmitted to a remote display device and can be uploaded, immediately or later, to a computer in a central facility for recording in a database, the results of soil evaluations conducted by the DCP can be made available to more people in less time. Thus personnel working a particular project will be more informed about the condition of soil being evaluated and will be able to make quicker and more informed decisions as to how work on the project should proceed.

In embodiments of the device of the present invention, an independent time/date stamp for each test can be provided. Further, to insure accuracy, embodiments of the device can be made such that the operator has a limited ability to interfere with or modify test results. The device of these embodiments can therefore limit the interaction of the operator with data collected to thereby better insure that the test details cannot be modified, either purposely or incidentally. In addition, the present embodiment can measure the time that it takes for the drop weight 25 to fall from the raised position to contact the anvil 24 in order to verify that the weight was raised to an appropriate height and that the fall of the weight 25 was unimpeded.

In some embodiments, the sensor 34 can measure the distance that the tip of the DCP travels into the soil, without being in physical contact with the DCP during operation. Such a system can advantageously protect the sensor device from exposure to the elements, and also the particularly the harsh conditions at a test or construction site. Previous attempts at independent or alternative measurement techniques, in the prior art, have involved equipment requiring actual physical connection or attachment to the DCP. Such prior art devices, as will be understood, are often subjected to harsh conditions permitting devices to bend, break or be otherwise damaged, causing diminution in accuracy or delay in completion of tests.

As shown in FIG. 2, the sensor assembly 31 features a transmitter that can relay data and other information about the test to a cooperative unit, such as a receiving unit 40 which is capable of interaction and/or communication with the operator or a computer. In a preferred embodiment, such communication or interaction is accomplished without using wires or other physical communication means that are prone to breakage and are often difficult to use without entanglement.

It will be understood by persons having ordinary skill in the art that the utilization of a non-contact device and method for incremental and overall distance measurement can eliminate the problems occurring due to having equipment exposed to the impacts and vibrations inherent in the dropping of a weight and its jarring contact with the anvil. The added benefits of automatic recordation of the details of tests, without operator access, provides a more independent verification of the performance of the test and its results.

The illustrated embodiments also have many benefits over prior systems including: electronic recordation of the cumulative penetration depth and the depth of the DCP after each blow by the drop weight 25; systematic recordation of the number of blows by the drop weight; time-stamping of data records; independent verification of data through software algorithms of associated handheld computing devices; and isolation of recordation devices to protect them from vibrations resulting from the drop weight of the DCP.

It will be seen in FIG. 2 that there are primarily three main components to the automated device of the present embodiment. The first component, as shown in FIG. 2A, is the sensor assembly 31 which consists of: an optical distance sensor 34 having a light source 38 and sensing means 39; data acquisition circuitry 35; a wireless transmitter 36 and a power supply 37. The sensor assembly 31 is mounted in a housing 32 that has a centrally located opening 33 to permit the shaft 20 and tip 23 of the DCP 10 to pass through the housing 32 and contact the soil S. As shown in FIG. 2, the housing 32 is placed directly on the soil to be evaluated.

The second main component of the automated device is a remote operator assembly 40. The remote operator assembly 40 consists of a wireless receiver 41 and an electronic processing device 42, such as a handheld computer or personal data assistant ("PDA"). It will be understood by persons having ordinary skill in the art that any manner of data collection and possessing device can be used here, without departing from the novel scope of the present invention. The wireless receiver 41, as illustrated, can record the incremental blowcount and distance information transmitted to it from the wireless transmitter 36 of the sensor assembly 31 and forward the information to a processing device 42. The processing device 42 can include means to present some or all information to the user of the device, such that the efficacy of the test can be determined periodically such that necessary changes or adjustments to the test can be made. The processing device 42 further serves as a data recorder for storing information for observation and reporting purposes. Alternative processing devices such as laptops computers or smart phones having electronic processors, storage units and display screens can alternatively, or additionally, serve as the processing device 42 without departing from the novel scope of the present invention. In addition, alternative means of communications between the sensor assembly 31 and the remote operator assembly 40 can be utilized without departing from the novel scope of the present invention. For example, Bluetooth® or equivalent wireless protocol technology, other short distance telemetry protocols, infrared transmitting and reading devices are contemplated for use in the device and method of the present invention. Further, other technological measuring means, including for example global positioning satellite systems ("GPS"), can be substituted or added to the device of the present embodiment without departing from the novel scope of the present invention. Such GPS systems can provide independent verification of the location of a particular job or soil evaluation and can additionally be used to verify the elevation of the drop weight or DCP in relation to the ground surface.

Figure 2B:
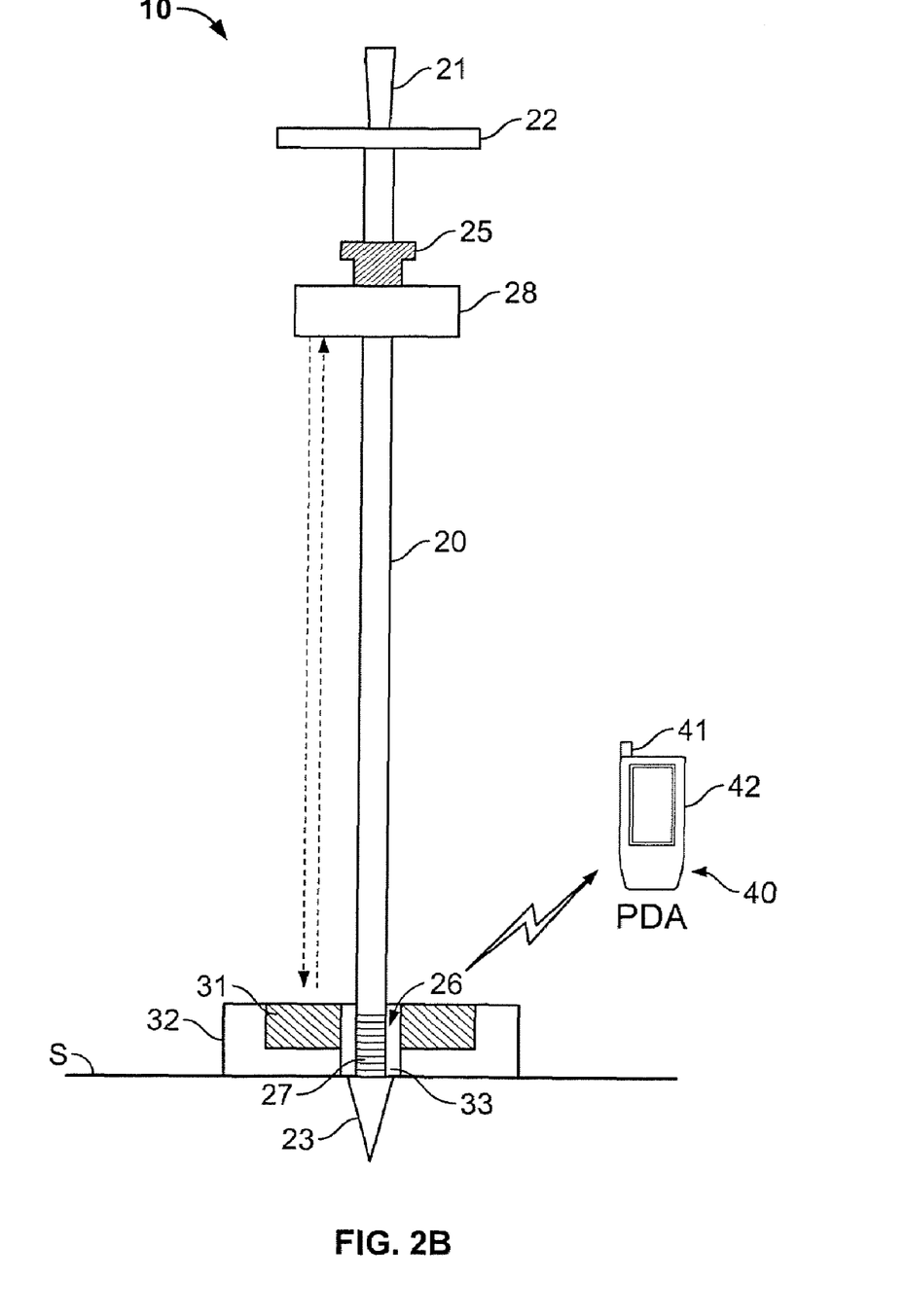
FIG. 2B is an elevational view of an alternative embodiment of a device made in accordance with the teachings of the present invention.

The third main component of the automated device of the embodiment shown in FIG. 2 is a sensor target 30, which in a preferred embodiment can be mounted to the shaft 20 of the DCP 10. While the sensor target illustrated in FIG. 2 is shown in one particular position on the shaft 20, those having ordinary skill in the art will understand that the target can be positioned in a number of different locations along the shaft 20 and can be adjustably fastened to the shaft by utilizing, for example, an adjustable collar having a locking pin, bolt or screw. The sensor target 30 allows the sensor 34 to determine the distance that the DCP 10 has traveled by measuring the distance between the sensor 34 and the target 30. In an alternative embodiment, as shown if FIG. 2B, a sensor 34 having, for example, a laser light source, can be employed to emit a narrow beam of concentrated light in the direction of the anvil 24, in a manner that enables the light to reflect off of the bottom surface of the anvil 24, and return to be read by a sensing means 39 configured to read and evaluate such light measurements. In this embodiment, use of the sensor target 30 is unnecessary because a laser light source is of sufficient intensity to be detected by the sensor 34, after being directed at the more non-reflective bottom surface of the anvil 24. A sensor target 30 may however be used in connection with the embodiment illustrated in FIG. 2B without departing from the scope of the present invention.

The present invention additionally provides a method of using the automated device in connection with a DCP 10. Such a method includes placing the housing 32 having the sensor assembly 31 at a fixed position on the ground surface S that is to be evaluated; positioning a DCP 10 having a sensor target 30 mounted to the elongated shaft 20, such that the target 30 is above the sensor 34; and aligning the sensor 34 in a vertical plane such that the sensor target 30 can be seen by the sensor 34. The initial vertical position of the DCP 10 can then be measured by detecting the distance between the sensor 34 and the target 30. This distance data is streamed, as an electronic signal, from the wireless transmitter 36 to the wireless receiver 41 mounted to the remote operator assembly 40. The electronic processing device 42 then monitors the signal as a value, in real-time, such that the value remains constant where the distance between the sensor 34 and the target 30 does not change. The actual test is then carried out with the DCP 10 by raising the drop weight 25 from a first position adjacent to the anvil 24 to a predetermined second position above the anvil 24 and then releasing the drop weight 25 from the second position to allow the weight to fall to the anvil 24. The contact of the weight 25 with the anvil 24 generates a standardized force that causes the penetrometer to move in a downward direction into the soil such that the distance between the target 30 and sensor 34 decreases. Optical sensor 34 then detects the new distance between it and the target 30; and data indicating the new distance between the two is broadcast by the wireless transmitter 36 to the receiver 41 of the remote operator assembly 40. The new distance is then transmitted to the electronic processing device 42 where it may be recorded and displayed.

Changes in the streaming value indicate that a blow has occurred, with the new repeating value representing the next distance; the difference between the new value and the previous value is the distance traveled resulting from the blow. By monitoring the total distance traveled by the DCP 10 and the number of blows made, the soil compaction can be determined. Determination can be made in at least one of two ways. First, by counting the total number of blows to travel a known distance, and comparing the number with the minimum required number for adequate soil compacting. Alternatively, the number of blows can be counted until the minimum required number is reached, and comparing the actual traveled distance to a known distance; a passing result occurring if the actual distance is less than the known distance. In addition, other soil properties may be inferred from a continuous record of blowcount versus penetration.

Figure 3:
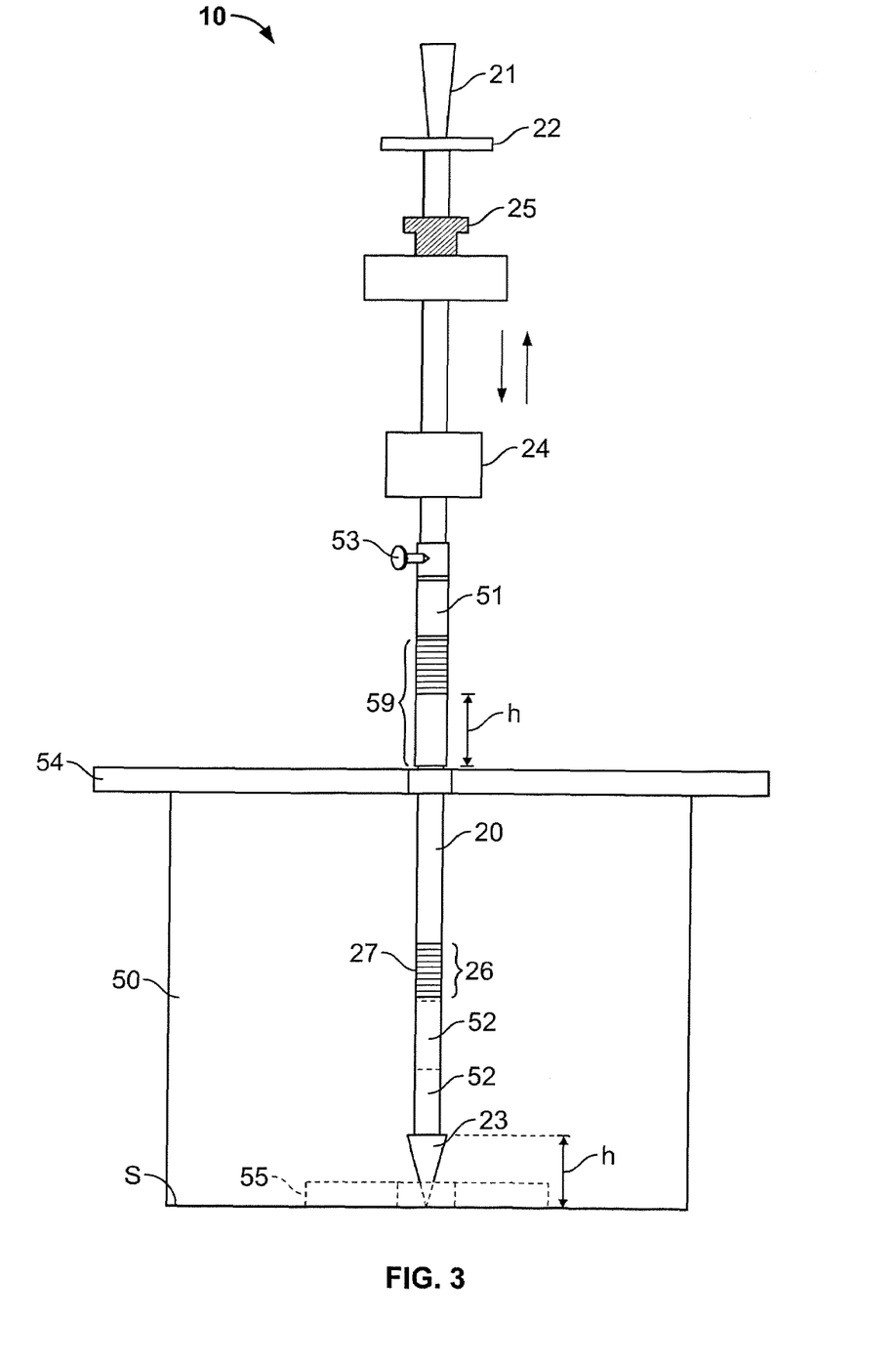
FIG. 3 is an elevational view of another embodiment of a device made in accordance with the teachings of the present invention; showing the use of a DCP in a "keyhole" application.

FIG. 3 illustrates an alternative embodiment of the present invention, which is intended to enable a DCP 10 to be used to evaluate the compaction of a ground surface S at the bottom of a keyhole opening 50, or other type of small excavations, where a remote reading from the surface is necessary or desired. The present invention features a DCP 10 having general characteristics as described above, in combination with additional components such as an adjustable collar 51 and/or shaft extension unit 52. As shown in FIG. 3, the adjustable collar 51 of this embodiment is adapted to fasten around the elongated shaft 20 of the DCP 10 between the anvil 24 and the second end of the shaft 20. Once a correct position for the collar 51 is determined, it may be fastened to the elongated shaft 20 in a fixed position by means of a locking pin, bolt or screw 53 such that the collar 51 will not slide down the shaft 20 when the drop weight 25 contacts the anvil 24 during the evaluation. The collar 51 can additionally feature cooperative graduations of comparable dimension to the markings of the graduated area on the elongated shaft near the tip.

In order to match the DCP 10 of this embodiment to the depth of the keyhole opening 50, the DCP 10 may additionally include one or more shaft extension units 52 that are capable of being fastened to one another at their ends or alternatively to the elongated shaft 20 or the conically shaped tip 23. When the appropriate number of shaft extension units 52 are used, it is intended that the DCP 10 will extend outside the opening of the keyhole 50 to such an extent that the adjustable collar 51 can be positioned in a manner that enables a portion of the collar to be in generally horizontal alignment with the opening of the keyhole 50. When this is accomplished, a bar, plate, or other apparatus 54 having a flat surface, can be placed across the top opening of the keyhole 50, such that the cooperative graduations of the collar 51 can be read against the top surface of the apparatus 54 spanning the opening. For convenience, the apparatus 54 spanning the keyhole 50 can be perforated to allow the DCP 10 to pass through it; or alternatively, can be positioned adjacent to the DCP 10 such that readings can be taken against the edge of the apparatus 54. This embodiment can further feature the use of a surcharge weight 55 to assist with the evaluation of compaction of the soil S. The surcharge weight 55 can be part of housing 32 or may be a separate component that can be fastened to the housing 32 or merely used on its own. In use, the surcharge weight 55 can be placed directly on soil S so that a single depth of penetration may be sufficient for more soil types, and a single blow-count criterion may likewise be made more nearly universal. As shown in FIG. 3, the surcharge weight features a centrally located opening 39 so that the shaft 20 and tip 23 of the DCP 10 are able to pass through the weight 55 and contact the soil S.

Figure 4:
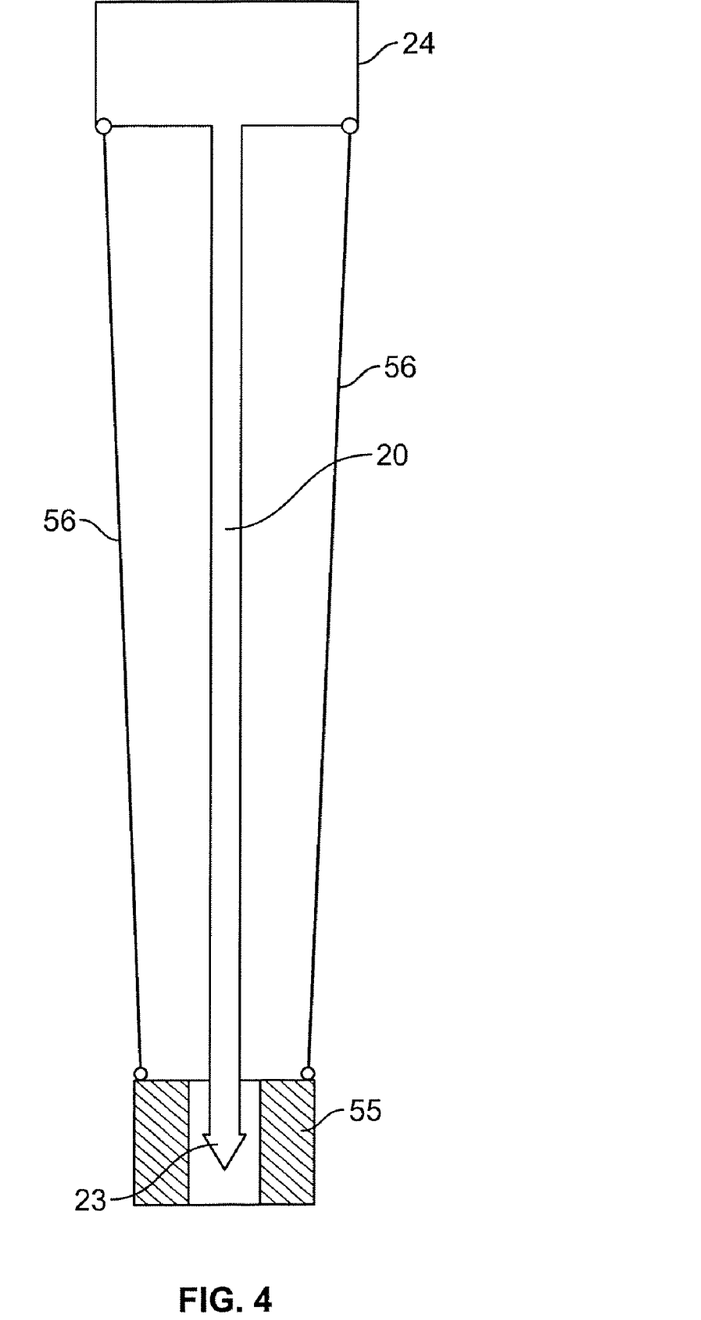
FIG. 4 is an elevational view of a further embodiment of a device made in accordance with the teachings of the present invention showing a device and method for placing and retrieving a surcharge weight and/or sensor assembly from the bottom of a keyhole when the device is used in connection with the embodiment demonstrated in FIG. 3.

Referring now to FIG. 4, a device and method of another embodiment of the present invention is shown for enabling a surcharge weight 55 to be placed or retrieved from the bottom of a keyhole opening 50. In this embodiment, flexible cables 56 of an appropriate length are used to attach the weight 55 to the penetrometer (for instance to the bottom of the anvil), so that the weight 55 hangs slightly below the tip 23. The cables 56 can be adjusted for various shaft lengths provided by the extensions described earlier. Once the surcharge 55 rests on the surface, further descent of the DCP 10 into the soil will result in slacking of the cables 56, and thus prevent interference with the DCP 10 operation. Upon completion of the test, withdrawal of the DCP 10 will automatically result in simultaneous retrieval of the surcharge weight 55. It will be further understood by a person having ordinary skill in the art that other connectors can be used instead of cables 56 without departing from the novel scope of the present invention.

Figure 5:
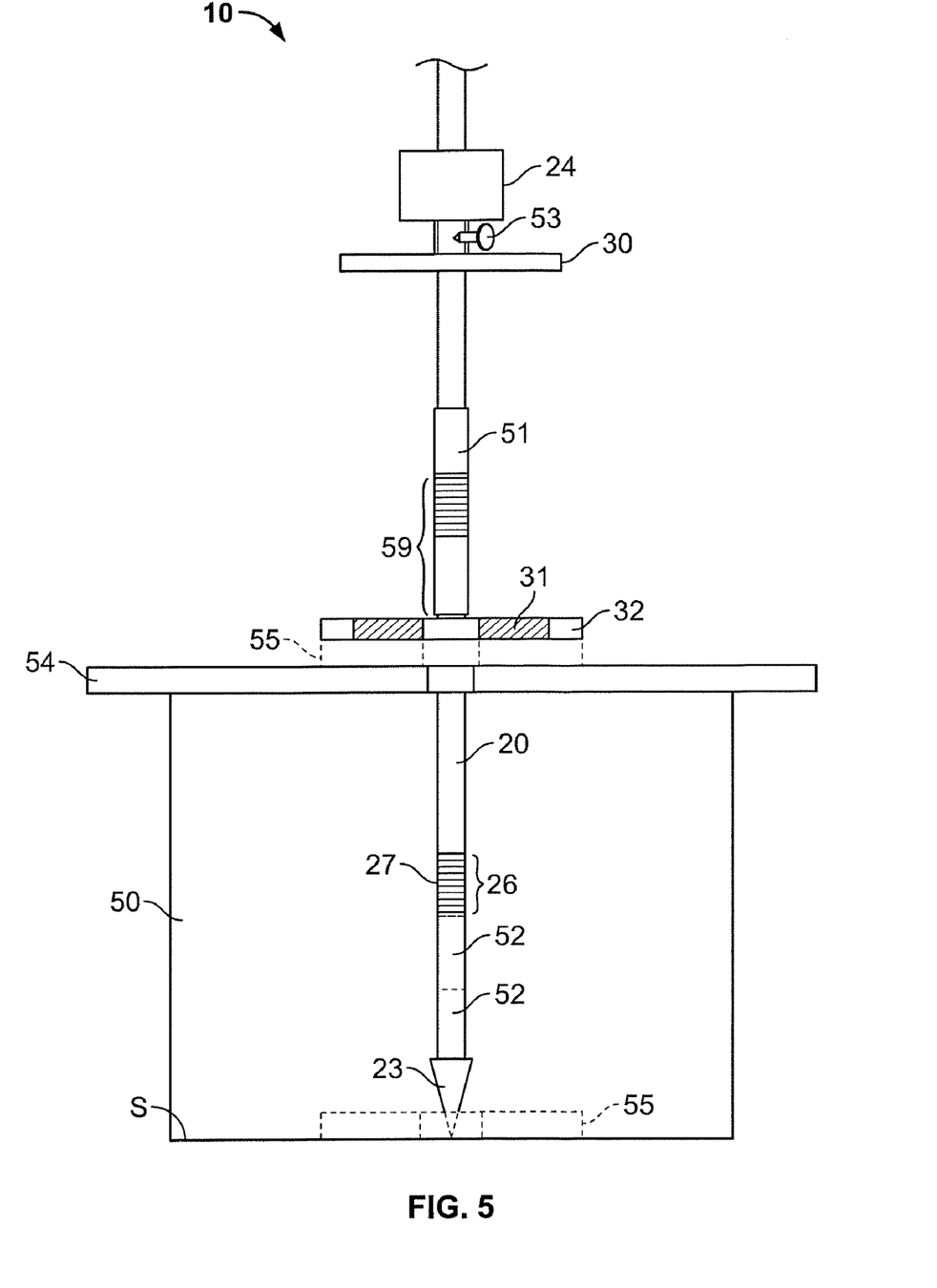
FIG. 5 is an elevational view of a further embodiment of a device made in accordance with the teachings of the present invention, showing a DCP used in a keyhole application together with an automated device and method where a sensor assembly is placed outside a keyhole opening.

FIG. 5 illustrates a further embodiment of the present invention featuring the use of DCP 10 in a keyhole application in combination with an automated method and device for recording and collecting data generated by the penetrometer. In this embodiment, the housing 32, having a sensor assembly 31, is positioned on top of an apparatus 54 that spans the open top of the keyhole 50. It will be seen that housing 32 can be placed either directly on top of apparatus 54 or on the top of a surcharge weight 55 positioned on top of apparatus 54. In this embodiment, an additional surcharge weight 55 can also be positioned on the ground surface S, at the bottom of the keyhole opening 50.

In operation of the embodiment shown in FIG. 5, the user of the DCP 10 positions the adjustable collar 51 such that the cooperative graduations 59 are in general horizontal alignment with the top surface of sensor assembly 31. Once this initial condition is established, the operator may then begin the evaluation process by raising and releasing the drop weight 25. While use of the automated data collection device and method of the present embodiment can enable the user of the DCP 10 to collect or evaluate the results of a particular test in full automatic mode, the location of the cooperative graduations 59 on the adjustable collar 51 makes it easy for visual verification to be manually performed as well. In addition, while the reflector plate 30 illustrated in FIG. 5 is shown to be mounted directly to the adjustable collar 51, this is just one possibility, and those persons having ordinary skill in the art will understand that the reflector plate 30 could be mounted to the DCP 10 without being fastened to the collar 51 without departing from the novel scope of the present invention.

Figure 6:
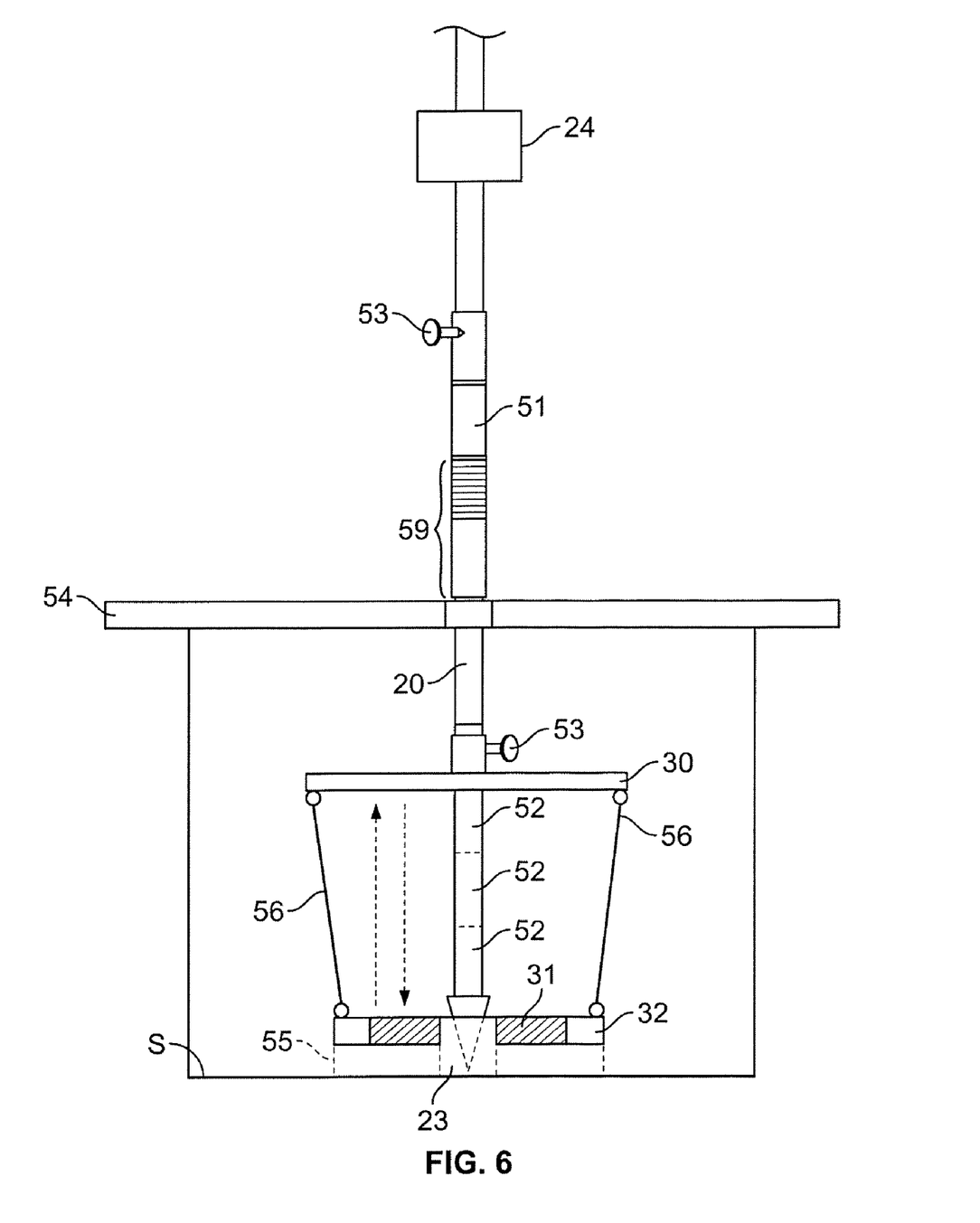
FIG. 6 is an elevational view of a further embodiment of a device made in accordance with the teachings of the present invention featuring the use of a DCP in a keyhole application together with an automated sensor assembly located within a keyhole opening.
Figure 7:
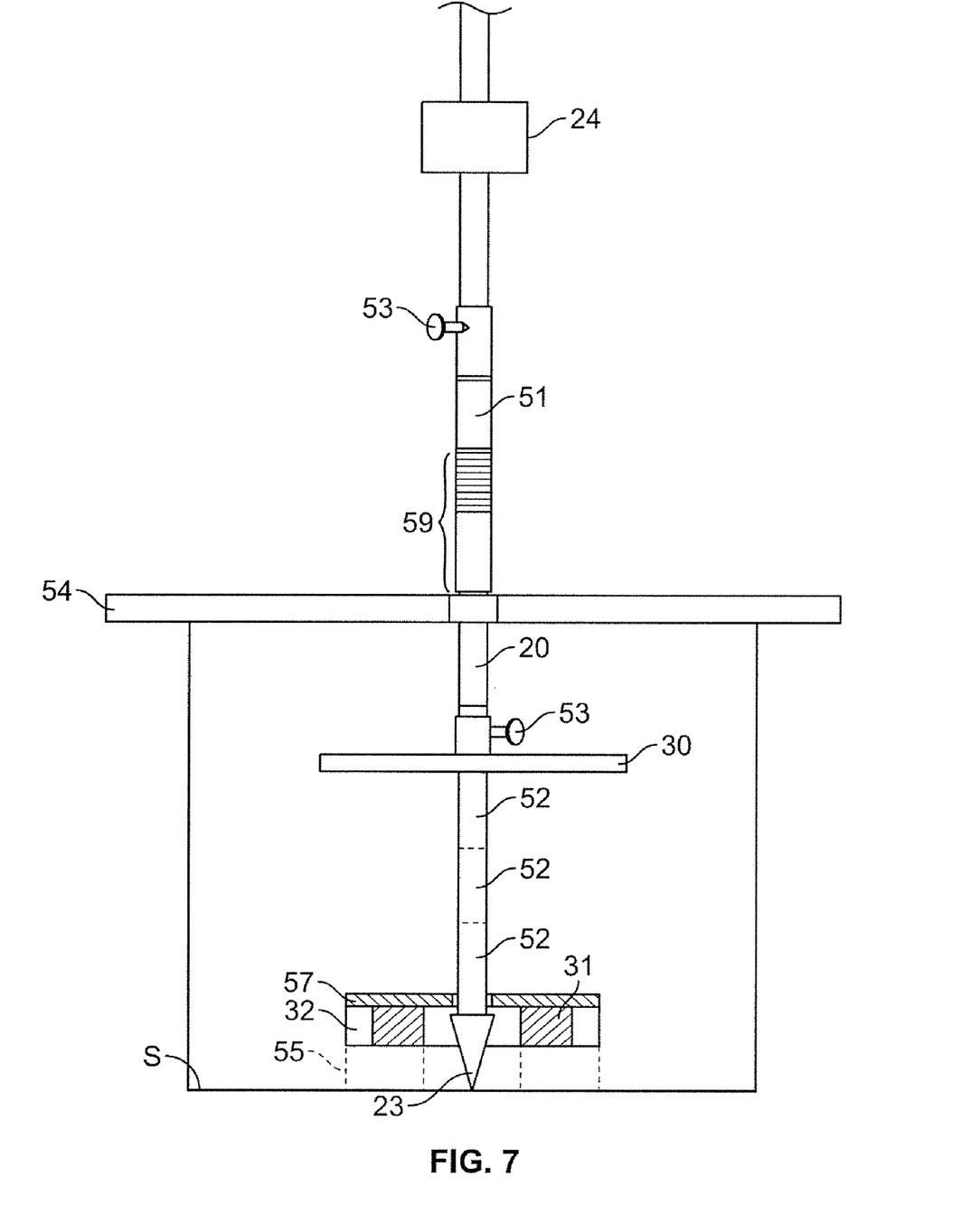
FIG. 7 is an elevational view of another embodiment of a device made in accordance with the teachings of the present invention featuring the use of a DCP in a keyhole application together with an automated sensor assembly.

FIGS. 6 and 7 illustrate additional embodiments of the present invention featuring a DCP 10 used in a keyhole application where the sensor assembly 31 is positioned within the keyhole 50 and proximate to the ground surface S. As shown in FIGS. 6 and 7, a housing 32 having a sensor assembly 31 can be positioned directly on the soil surface S or can instead be positioned on the top of a surcharge weight 55 positioned on surface S. FIG. 6 additionally shows a device and method for remote placement and retrieval of the housing 32 and/or surcharge weight 55, similar to those previously described for remote placement and retrieval of the surcharge weight 55 (See FIG. 4). In FIG. 6, the sensor target 30 is fixed to the shaft 20, or a shaft extension unit 52, at a suitable height above the tip 23. At least one flexible connector 56 attaches the housing 32 (and surcharge weight 55 if appropriate) to the sensor target 30, such that the withdrawal of the DCP 10 from the keyhole 50 will automatically result in simultaneous retrieval of the sensor assembly 31 (and surcharge weight 55 if used). The sensor target 30 thus acts as a point of attachment for the automated device 31 and surcharge weight 55.

Figure 7A:
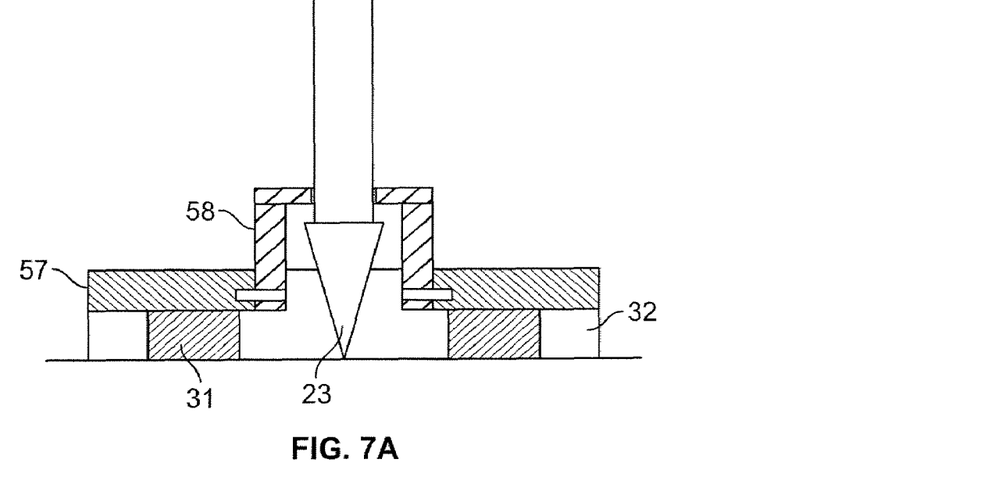
FIG. 7A is a close-up broken elevational view of an insert for placing or retrieving the sensor assembly and/or surcharge weight form a keyhole opening.

An alternative method for remote lowering and retrieval of the sensor assembly 31 and/or surcharge weight 55 is shown in FIGS. 7 and 7A. In this embodiment a flange 57 or insert 58 is fastened to the housing 32 having the sensor assembly 31. The flange 57 and insert 58 are sized to allow free passage of the shaft 20 or shaft extension unit 52, but not the tip 23. Such an arrangement will need to take account of whether the combined height of the housing 31 and surcharge weight 55 is greater or less than the height of the tip 23. In circumstances where the tip 23 has a greater height than the housing 31, as shown in FIG. 7A, an insert 58 can be affixed to the flange 57, in order to accommodate for the height differential. The embodiment illustrated in FIGS. 7 and 7A thus permits lowering the sensor assembly 31 and/or surcharge weight 55 to the surface, whereupon normal operation of the DCP 10 can proceed. Upon withdrawal of the DCP 10, the top of the cone 23 will engage with the flange 57 or insert 58, resulting in simultaneous retrieval of the sensor assembly 31 and/or surcharge weight 55.

Figure 8:
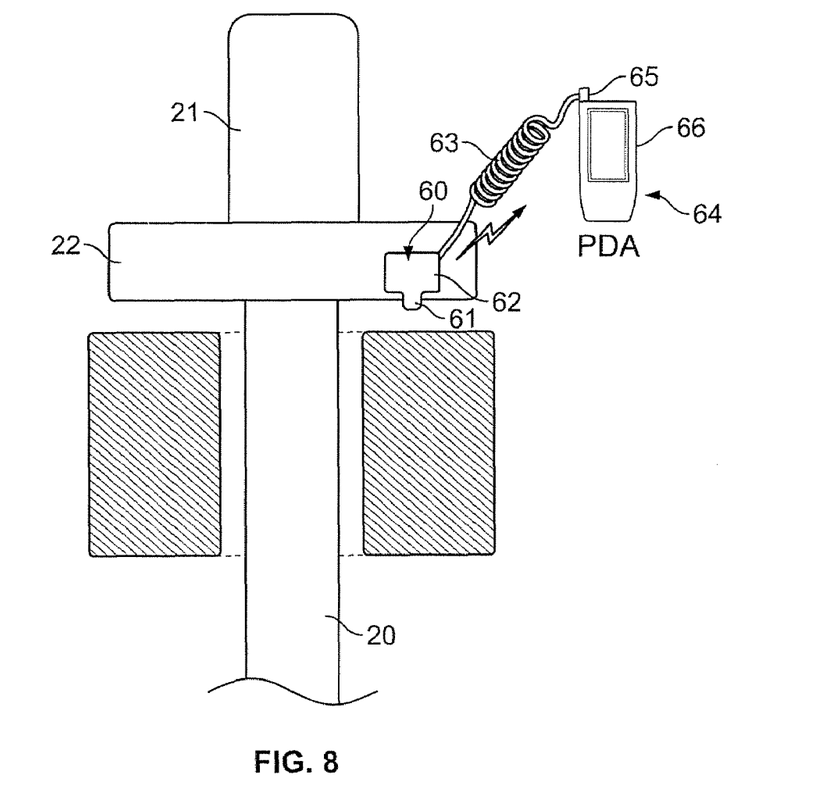
FIG. 8 is a cut-away elevational view showing an automated weight-position detection assembly of the present invention.

Another embodiment of the present invention is featured in FIG. 8. In this embodiment an automated device and method is shown for detecting when the drop weight 25 of a DCP 10 has been raised into the correct position before being released to contact the anvil 24. As shown in FIG. 8, the device features a weight detection assembly 60 having a detector 61 and transmission element 62, and a remote operator assembly 40 having a receiver 41 and an electronic processing device 42. While FIG. 8 shows a the transmission element 62 and receiver 41 to be connected by a flexible wire for transmission of signals to the receiver 41, it will be understood by those having ordinary skill in the art that wireless transmission may be used to broadcast a signal from the transmission element 62 to the receiver 41 without departing from the novel scope of the present invention.

As shown in FIG. 8, the detection assembly 60 is positioned on the flange 22 of the penetrometer, such that the detector 61 is adapted to sense the presence of the drop weight 25 when the weight is raised to a particular position above the anvil 24. Once the weight 25 is raised into this position, the detector 61 is actuated and the transmission element 62 broadcasts a signal to the receiver 41 of the remote operator assembly 40. While it is contemplated that the receiver 41 and electronic processing device 42 of this embodiment are the same as that previously described, a separate receiver 41 and processing device 42 can be used without departing from the spirit or scope of the present invention.

In the present embodiment, there are a number of different means by which the drop weight 25 can be detected. The first is by physical contact, in which the detector 61 is a switch that is actuated when the weight is raised to a point on the shaft at which the detector is depressed. The switch of the detector 61 may be a momentary electric switch or an optical or ultrasonic-proximity switch that is adapted to sense when the weight 25 is a particular distance away. Alternatively, when the drop weight 25 comprises a magnetic field, the detector 61 can be an inductive sensor that senses when the drop weight 25 is at a particular distance away, by detecting the magnetic field. Such sensing can include, for example, determining the amount of time it takes light or sound energy transmitted by the switch to be reflected off of weight 25. Further, the use of laser or infra-red technologies can also be employed in connection with this embodiment, without departing from the novel scope of the present invention.

In the use of the device illustrated in FIG. 8, a method is provided for automatically detecting the presence of a drop weight 25 that is mounted to a DCP. The method includes raising the drop weight 25, from a first position adjacent to the anvil 24 to a second position above the anvil 24; detecting the presence of the drop weight 25 in the second position by a weight detection assembly 60; generating an electronic signal indicating that the weight 25 is present in the second position; transmitting the electronic signal to a reception element 41, of a remote operator assembly 40 (having for example an electronic processing device 42); releasing the drop weight 25, from the second position above the anvil 24, such that the weight 25 is permitted to fall in a direction towards anvil 24; and detecting the absence of the drop weight 25 in the second position upon the release of weight 25. The method can further include timing the fall of the drop weight from the second position to the anvil in order to verify that the weight was raised to its proper elevation on the shaft and that it was not interfered with after being released.

The present disclosure includes that which is contained in the appended claims, as well as that of the forgoing description. Although, this invention has been described in its preferred form with a certain degree of particularity, it is understood that the present disclosure of the preferred form has been made only by way of example, and that numerous changes in the details of the elements, compositions and the combination of individual ingredients may be resorted to without departing from the spirit or scope of the invention.

What is claimed is:

1. A dynamic cone penetrometer ("DCP") for automated evaluation of soil compaction, comprising:
    an elongated shaft having a first and second end, the first end having a flange and a handle adjacent to the flange, the flange extending in a direction generally perpendicular to the elongated shaft;
    a tip at the second end of the elongated shaft;
    an anvil fixedly mounted to the elongated shaft between the first and second end;
    a drop weight slideably mounted to the elongated shaft such that the weight is moveable along the shaft between the flange and the anvil; and
    an automated device for collecting and processing compaction data and allowing the user to monitor the compaction data before and after processing, the automated device having a sensor assembly with distance sensing means, data acquisition means, and a transmitter, the sensor assembly mounted in a housing having a centrally located opening, the opening suitable for permitting the second end of the elongated shaft to extend through the housing; the automated device further having an operator assembly having a display device, a recording device, a receiver for receiving data from the transmitter and a processing device in communication with the receiver for processing the data communicated to the receiver and communicating the processed data to the recording device and the display device, the display device of the operator assembly displays data generated from the DCP.

2. The dynamic cone penetrometer of claim 1 wherein the distance sensing means is an optical distance sensor adapted to detect light from a light source associated with the optical distance sensor.

3. The dynamic cone penetrometer of claim 1 wherein the distance sensing means is an ultrasonic distance sensor adapted to detect sound from a sound source associated with the ultrasonic distance sensor.

4. The dynamic cone penetrometer of claim 1 wherein the processing device is from a group consisting of a handheld computer, a laptop computer, a cell phone and a personal digital assistant ("PDA").

5. The dynamic cone penetrometer of claim 1 wherein the transmitter of the automated device is from a group consisting of a radio frequency transmitter, infrared light transmitter, Bluetooth® or equivalent wireless protocol signal transmitter and other short range telemetry protocol transmitter.

6. The dynamic cone penetrometer of claim 1 wherein the display device of the operator assembly displays data generated from the DCP in real-time.

7. The dynamic cone penetrometer of claim 1 wherein the operator assembly is detachable from the DCP.

8. The dynamic cone penetrometer of claim 1 wherein the transmitter of the automated device transmits data to an electronic processing device residing in a remote location relative the DCP, the remote processing device having a receiver for receiving data from the transmitter, a display device and a recording device, the remote processing device processing the data communicated to the receiver and communicating the processed data to the recording device and the display device, the display device of the remote processing device displaying data generated from the DCP in real-time.

* * * * *